(12) United States Patent
Sofie

(10) Patent No.: US 6,926,010 B1
(45) Date of Patent: Aug. 9, 2005

(54) DEVICE FOR COATING DENTAL FLOSS WITH TOOTHPASTE

(76) Inventor: Walter Francis Sofie, 441 VanDyke Ave., St. Paul, MN (US) 55119

( * ) Notice: Subject to any disclaimer, the term of this patent is extended or adjusted under 35 U.S.C. 154(b) by 224 days.

(21) Appl. No.: 10/404,577

(22) Filed: Apr. 2, 2003

(51) Int. Cl.[7] .............................................. A61C 15/00
(52) U.S. Cl. ........................ 132/322; 132/314; 53/431
(58) Field of Search ................................ 132/322, 324, 132/325, 328, 329, 314; 222/192; 53/428, 53/431

(56) References Cited

U.S. PATENT DOCUMENTS

| | | | | |
|---|---|---|---|---|
| 1,466,982 A | * | 9/1923 | Bailey ........................ 132/314 |
| 1,733,114 A | * | 10/1929 | Brennan ...................... 132/314 |
| 3,830,247 A | * | 8/1974 | Kaphalakos ................. 132/322 |
| 4,019,522 A | * | 4/1977 | Elbreder ...................... 132/322 |
| 4,428,389 A | * | 1/1984 | Sanchez Cordero ........ 132/325 |
| 5,065,861 A | * | 11/1991 | Greene et al. ............. 206/63.5 |
| 5,076,302 A | * | 12/1991 | Chari .......................... 132/325 |
| 5,582,195 A | * | 12/1996 | Nagel .......................... 132/324 |
| 6,705,328 B1 | * | 3/2004 | Ramirez ...................... 132/322 |

* cited by examiner

Primary Examiner—Kevin Shaver
Assistant Examiner—Stephanie L. Willatt
(74) Attorney, Agent, or Firm—Thomas B. Tate

(57) ABSTRACT

A device for coating dental floss with toothpaste. The device has a main body which has a chamber for containing a floss spool and a female stem to receive a tube of toothpaste, a floss spool disposed within the chamber, a threaded male stem, a spool chamber cover, a floss passage block which has two openings of different sizes, and a cut-off tang.

1 Claim, 3 Drawing Sheets

DEVICE FOR COATING DENTAL FLOSS WITH TOOTHPASTE

BACKGROUND OF THE INVENTION

The field of the invention is devices for coating dental floss with toothpaste.

No prior art devices are known to exist.

SUMMARY OF THE INVENTION

The device allows dental floss to be coated with toothpaste as the floss is pulled through the openings in the main body of the device.

Advantages of the invention are that coating dental floss with toothpaste enhances the flossing experience by applying the decay fighting and abrasive ingredients of toothpaste between the teeth during flossing, thus contributing to the prevention of tooth decay and gum disease.

DETAILED DESCRIPTION OF THE INVENTION

Figure 1:
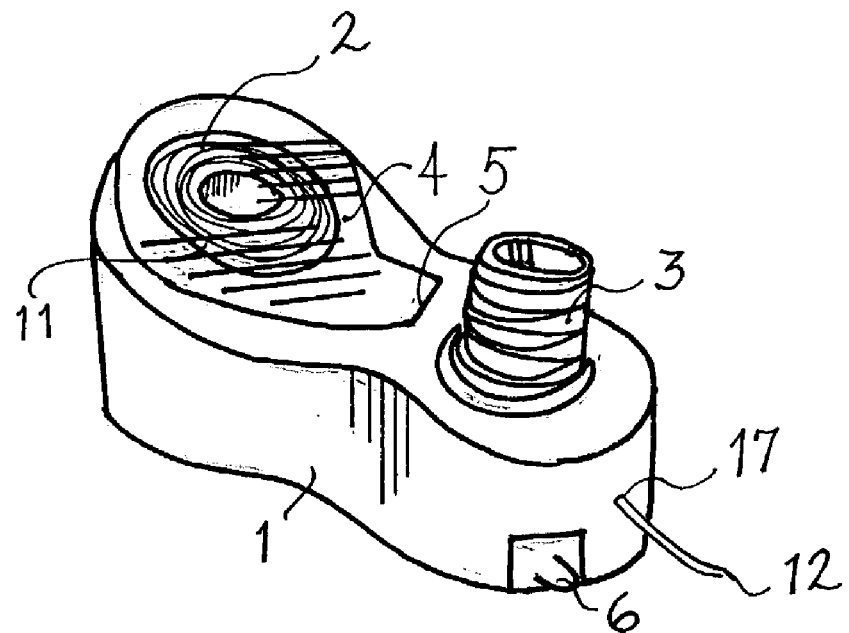
FIG. 1 is a perspective view of the top and side of the invention.
Figure 2:
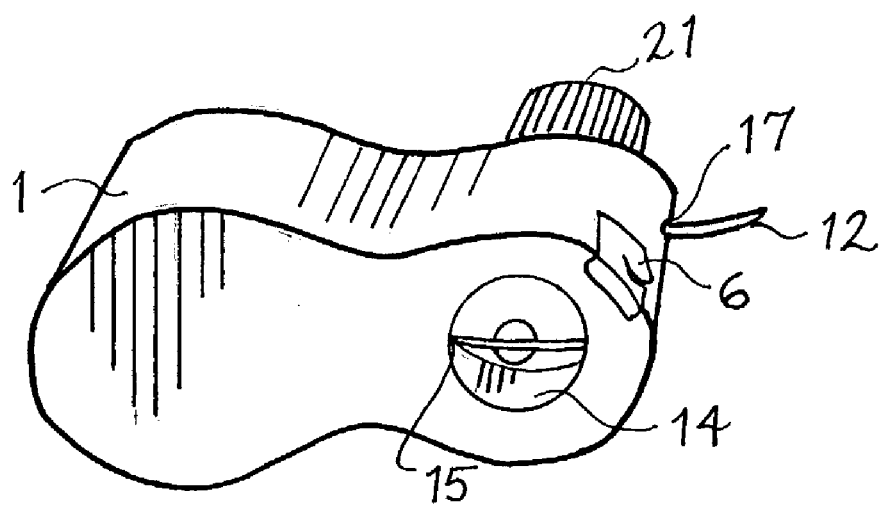
FIG. 2 is a perspective view of the bottom and side of the invention.
Figure 3:
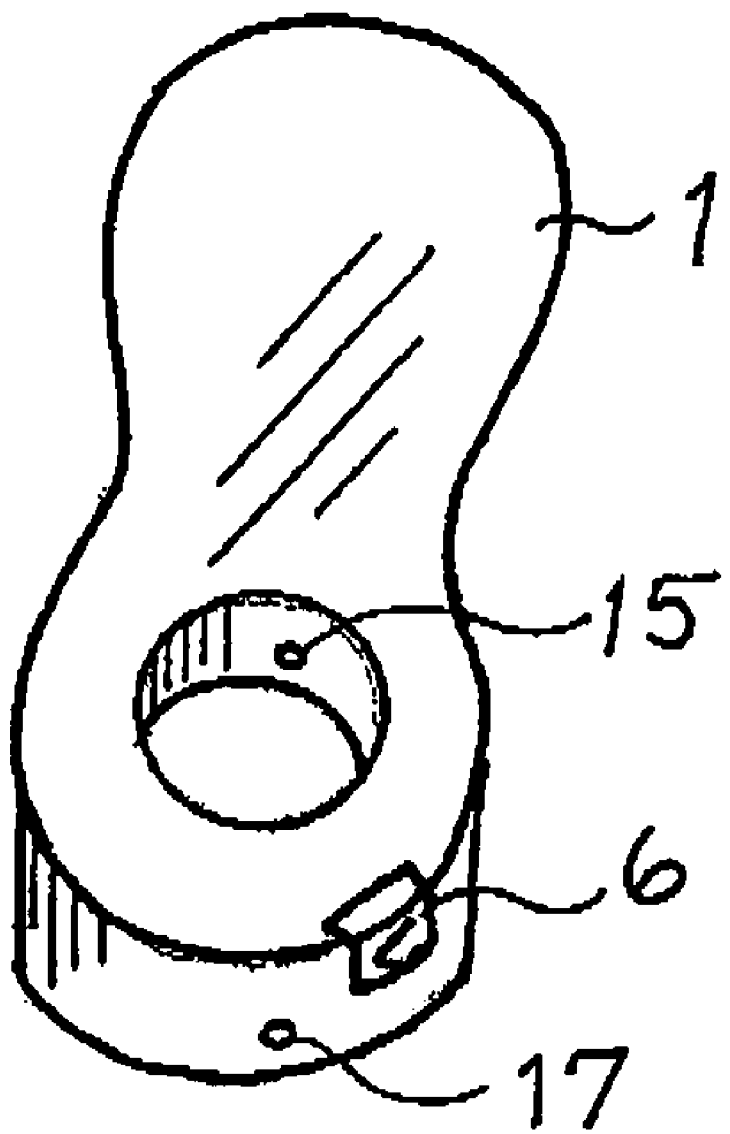
FIG. 3 is a bottom perspective view with the dental floss removed to more clearly show the openings through which the floss passes.
Figure 4:
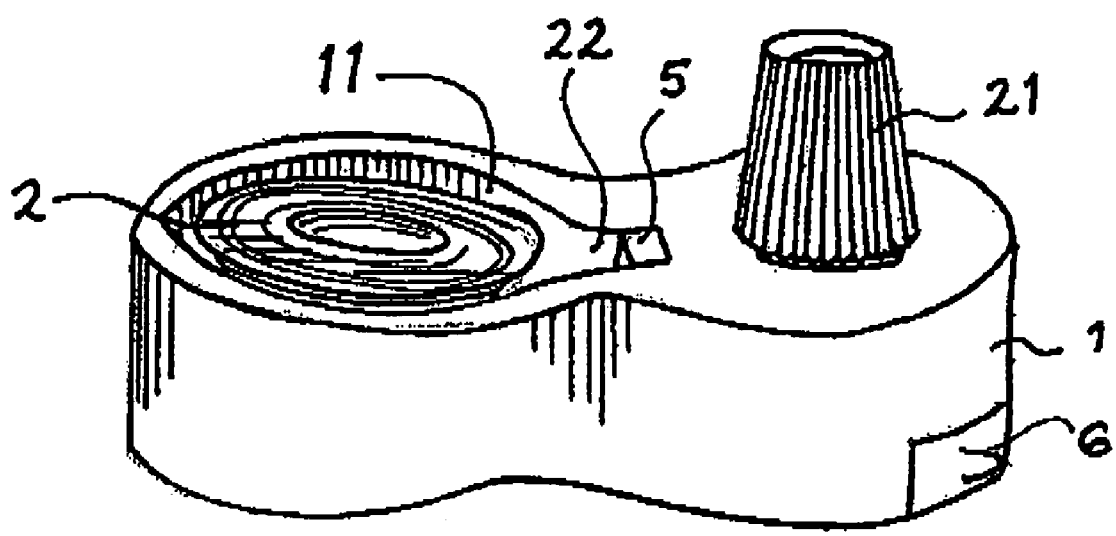
FIG. 4 is a side view with the spool chamber cover removed to more clearly show the narrow diameter passageway and the floss passage block.

The invention is a device for coating dental floss with toothpaste. The device comprises a main body 1, a floss spool 2, a threaded stem 3, a spool chamber cover 4, a floss passage block 5, and a floss cut-off tang 6.

The main body 1 is formed of molded plastic. A floss spool chamber 11 is formed into the top of the main body 1. The chamber 11 is generally circular but has at one end a narrow diameter passageway 22 through which the dental floss 12 passes. A threaded female inlet 14 is formed into the bottom of the main body 1. A conventional toothpaste tube (not shown) can be screwed into the female inlet 14 and remain in position for as long as there is toothpaste in the tube.

The floss spool 2 is molded of plastic and is a typical double-flanged (bobbin type) spool upon which a roll of dental floss 12 is mounted. The floss spool 2 is disposed within the spool chamber 11, which accommodates the vertical and horizontal movements of the floss 12 as it is unwound. The bottom surface of the spool 2 rides upon the floor of the spool chamber 1, thus providing a certain amount of frictional spool braking.

The male stem 3 is a threaded plastic molded component which is affixed to and projects upwardly from the main body 1. A standard toothpaste tube cap 21 can be fitted over the male stem 3.

The spool chamber cover 4 fits over the spool chamber 11 to serve as a top containment for the floss spool 2. The chamber cover 4 has a major surface with a molded ridge around its perimeter that contacts the main body 1 and fits into the spool chamber 11. The cover 4 has a stem projecting downwardly to fasten it to the main body 1 inside the spool chamber 11, but this stem does not serve as an axle for the floss spool 2. The spool chamber cover 4 is made of molded tinted clear plastic to allow the user to visibly observe the remaining floss levels.

The floss passage block 5 is a solid rectangular molded plastic part which is fitted into the narrow diameter passageway 22 which serves as a receiving cavity formed within the main body 1. A hole 15 at the center of the block 5 is sized so that the floss 12 passes therethrough without any void space, thus eliminating the possibility of toothpaste backflowing into the spool chamber 11. The floss exit hole 17 in the main body 1, which is aligned in a straight line with hole 15, is larger and preset a pressure differential, thus assuring that there is no backflow of toothpaste into the spool chamber 11. The coating of the dental floss 12 with toothpaste occurs in the area between the female inlet 14 and the male stem 3. The cap 21 of the toothpaste tube is on as floss 12 is drawn through holes 15 and 17 and the toothpaste tube is squeezed, thus coating the floss 12 with toothpaste. When coating of floss 12 is not needed, the cap 21 can be removed so that toothpaste can flow through the male stem 3 onto a toothbrush in the conventional way.

The floss cut-off tang 6 is a metal stamped component of the type commonly used on dental floss containers in order to allow a given length of dental floss 12 (in the case of this invention, toothpaste-coated dental floss) to be severed for use. The tang 6 is molded into the main body 1.

Although certain materials are recited in this specification, these are included as illustrations of the best mode for carrying out the invention, and not by way of limitation.

I claim:

1. A device for coating dental floss with toothpaste, said device comprising:

a main body having formed therein a cavity which defines a floss spool chamber, a small diameter passageway through which dental floss can pass, and a threaded female inlet adapted to receive a toothpaste tube;

a floss spool disposed within said floss spool chamber;

a threaded male stem affixed to and projecting upwardly from said main body;

a spool chamber cover fastened to said main body, said cover being positioned above said floss spool chamber;

a floss passage block which is fitted into a receiving cavity within said main body, said block having a small opening at the end of said main body which is proximal to said floss spool chamber, a larger opening being formed into said main body at the end of said main body which is distal to said spool chamber, said small opening and said larger opening allowing said dental floss to pass therethrough and be coated with toothpaste when said toothpaste tube is squeezed while said dental floss is passing between said small opening and said larger opening;

a floss cut-off tang molded into said main body.

* * * * *